(12) United States Patent
Gegner et al.

(10) Patent No.: US 8,423,381 B2
(45) Date of Patent: Apr. 16, 2013

(54) PATIENT MONITOR WITH INTEGRATED CLOSED LOOP CONTROLLER

(75) Inventors: Guenter Gegner, Tuebingen (DE); Rolf Neumann, Calw (DE); Gerhard Tivig, Nufringen (DE); Halald Greiner, Nufringen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 214 days.

(21) Appl. No.: 12/922,879

(22) PCT Filed: Mar. 11, 2009

(86) PCT No.: PCT/IB2009/051018
§ 371 (c)(1),
(2), (4) Date: Sep. 16, 2010

(87) PCT Pub. No.: WO2009/115949
PCT Pub. Date: Sep. 24, 2009

(65) Prior Publication Data
US 2011/0015944 A1 Jan. 20, 2011

(30) Foreign Application Priority Data
Mar. 17, 2008 (EP) .................................... 08102663

(51) Int. Cl.
*G06Q 50/00* (2012.01)

(52) U.S. Cl.
USPC ............................................................ 705/2

(58) Field of Classification Search .. 705/2; 128/204.23
See application file for complete search history.

(56) References Cited

U.S. PATENT DOCUMENTS

| | | | |
|---|---|---|---|
| 5,365,922 A | 11/1994 | Raemer | |
| 6,186,142 B1 | 2/2001 | Schmidt et al. | |
| 6,192,883 B1 | 2/2001 | Miller, Jr. | |
| 6,557,553 B1 | 5/2003 | Borrello | |
| 7,008,380 B1 | 3/2006 | Rees et al. | |
| 2006/0266355 A1 | 11/2006 | Misholi | |
| 2007/0179349 A1 | 8/2007 | Hoyme et al. | |

FOREIGN PATENT DOCUMENTS

WO 2006075016 A1 7/2006

*Primary Examiner* — John Pauls

(57) ABSTRACT

The invention concerns a system for monitoring and controlling a patient (1), with a patient sensor (2) for capturing a patient signal, and a user interface (6) for providing a user with information on the captured patient signal, wherein the system comprises an integrated closed loop controller (4) which is fed with the patient signal and which controls a patient treating device (5) for treating the patient (1). Thus, an easy and efficient way of monitoring and controlling a patient is provided.

18 Claims, 1 Drawing Sheet

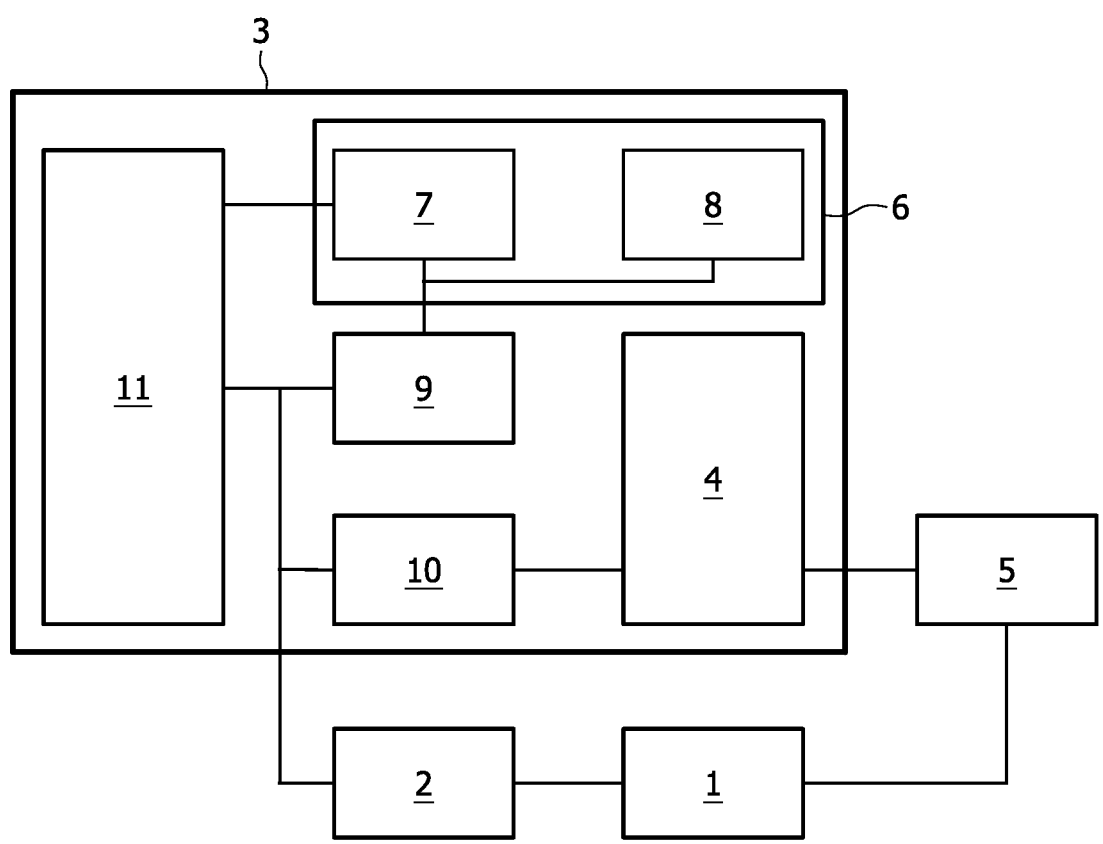

PATIENT MONITOR WITH INTEGRATED CLOSED LOOP CONTROLLER

FIELD OF THE INVENTION

The invention relates to the field of patient monitoring, and especially to combined patient monitoring and controlling a patient's physiological variable via a closed loop controller.

BACKGROUND OF THE INVENTION

Patient monitors are widely used in hospitals, especially in intensive care units and in premature infant wards. With such patient monitors one or typically multiple physiological variables are collected, processed if necessary and displayed to a user, like a care giver. Further, in general, patient monitors are also adapted for providing alarms if one or more of the collected variables exceed a respective predefined threshold.

A patient monitor is defined by comprising the following features:
  Measure at least one physiological signal, and
  Alarming capability for at least one measured signal and/or at least one interfaced physiological signal.

Further, a patient monitor may comprise one or more of the following features:
  At least one external signal to control external equipment, i.e. medical equipment for treating the patient.
  User interface possibilities to visualize measured and interfaced physiological signals.
  Trending possibilities for measured and interfaced physiological signals.
  Possibilities to analyze actual and trended measured and interfaced physiological signals, i.e. with a clinical decision support system.
  Possibilities to interact with the user and let the user enter data and comments of physiological and non-physiological data manually.
  Infrastructure to transfer captured and processed data to a wired or wireless connected medical system solution, e.g. a central station, a hospital information system, an electronic medical record.

A patient monitor does not have to be arranged in one single device common for all functions but can be a system with distributed units.

Further, physiological closed loop systems are known which use a patient variable for the control algorithm to calculate a signal for treating a patient. This often has the limitation that any disturbance on that specific patient signal results in either the inability to perform a control adjustment or, even worse, the control adjustment made is in the false direction. In a physiological closed loop system the transfer functions of a patient treating device with which a patient is treated, the patient itself and sometimes also the measurement of the patient variable are not constant and influenced by several external factors.

In principle, an automatic closed loop system shall reduce the work load of the care givers by partially replacing their actions with regard to the adjustments of the delivery of oxygen, medication or other treatment of the patient. However, actually regularly checking the patient's reactions to changes in the treatment of the patient are necessary, which is laborious for the care givers and can be annoying for the patient. For this and other reasons, the acceptance of the physiological closed loop systems is still low.

SUMMARY OF THE INVENTION

It is an object of the invention to provide an easy and efficient way of monitoring and controlling a patient.

This object is achieved by a system for monitoring and controlling a patient, with
  a patient sensor for capturing a patient signal, and
  a user interface for providing a user with information on the captured patient signal, wherein
  the system comprises an integrated closed loop controller which is fed with the patient signal and which controls a patient treating device for treating the patient.

Accordingly, it is an essential feature of the invention, that a closed loop controller is integrated into the patient monitor. This is a totally new approach, since conventionally closed loop controllers have always been arranged parallel to the patient monitor or in series with the patient monitor. While a parallel arrangement of the closed loop controller and the patient monitor requires additional sensor equipment, an arrangement in series does not provide for optimal patient signals for at least the closed loop controller or the patient monitor, respectively.

It is to be noted that in the context of the present invention, the term "patient" does not only apply to human beings but also to animals. Further, the term "patient" does not mean that the respective person/animal is disease-ridden and, thus, also healthy persons who make part of a medical system will be referred to as "patients".

According to a preferred embodiment of the invention, the system comprises a monitoring processer for processing the patient signal and for outputting processed data to the user interface, and further comprises a control processer for processing the patient signal and for outputting processed data to the closed loop controller, wherein the monitoring processer and the control processer are fed with the same patient signal in the same pre-processing state. This means that the patient signal can be provided to the monitoring processor and the control processor in a "raw" state, i.e. in a state which is only pre-processed in such a way which does not affect the further processing adversely. In case of an arrangement of the patient monitor and the closed loop control in series, this is not possible since the signal which is first fed to the patient monitor and processed by the patient monitor is not optimally suited for the open loop controller any more, and vice versa.

Further, according to a preferred embodiment of the invention, the system comprises an alarming unit which is fed with the patient signal and which is adapted for providing common alarm conditions for monitoring and controlling. Thus, the invention provides for the possibility of alarm prioritization which means that no separate alarms for monitoring and controlling, respectively, need to exist any more. Especially, this means that a combined alarming system for physiological vital signs alarms and closed loop alarms is possible. As a result, multiple alarms, caused separately by the patient monitor on the one hand and caused by the closed loop controller on the other hand can be avoided.

According to a preferred embodiment of the invention, the user interface is adapted for indicating and/or inputting monitoring data and control data. With respect to this, it is especially preferred that the user interface is adapted for requesting the user to input external data required as input data for the closed loop controller. This means that in such a case the closed loop controller becomes a controller of an open loop which requires external data input. This is especially advantageous in cases in which due to deviations of the collected patient signal from an expected signal correct controlling cannot be guaranteed for any more.

Above mentioned object is further met by a method for monitoring and controlling a patient, comprising the following steps:
    capturing a patient signal,
    providing a user with information on the captured patient signal,
    feeding a closed loop controller with the patient signal, and
    controlling a treatment of the patient with the closed loop controller.

Preferred embodiments of the system according to the invention result from the preferred embodiments of the method according to the invention as described above.

Especially, according to a preferred embodiment of the invention, the patient signal is processed for a monitoring purpose and output as processed data to the user, the patient signal is processed for a control purpose and output as processed data to the closed loop controller, wherein processing the patient signal for the monitoring purpose and processing the patient signal for the control purpose are bases on the same patient signal in the same pre-processing state.

Further, according to a preferred embodiment of the invention, common alarm conditions for monitoring and controlling are determined. Furthermore, it is preferred that for indicating and/or inputting monitoring data and control data a common user interface us used. With respect to this it is especially preferred that a user is requested to input external data required as input data for the closed loop controller via the common user interface.

Another preferred embodiment of the invention comprises the steps of controlling the treatment of the patient based on an input value, comparing the input value to an output value of the captured patient signal, and generating a further action if the output value deviates from an expected output value by more than a predefined amount. Accordingly, this preferred embodiment of the invention provides for regularly checking the control function of the control process. In case the patient's reaction to the treatment determined by the closed loop controller is not adequate any more, further action can be taken. Especially, it is preferred that the further action is an alarm and/or fallback to an open loop control. The latter means that a user, like a care giver, is requested to input external data in order reestablish a reliable and adequate controlling of the patient's physiological variable. With respect to this, according to a preferred embodiment of the invention, the input value is varied intentionally.

Accordingly, the measure according to this preferred embodiment of the invention overcomes prior art limitations by using an adaptive approach to react on changes of the transfer function of the patient. Moreover, this measure comprises means to alert the care giver of changes in the patient transfer function that might be indicative of conditions that the caregiver has to react upon. Thus, the basic principle is to use the feedback on the patient variable side as response to changes on the patient treatment device to supervise the whole control system.

With other words, the invention relates to combining the measurement and processing of the input variables and the patient variable as input to the control algorithm. This takes use of the advantages of immediate real-time access to the raw input signals, the possibility of optimized algorithms for closed loop control and vital signs processing, a combined alarming system for physiological vital signs alarms and closed loop alarms, synchronous data capturing in a patient data base, a unique user interface for vital signs and closed loop controller user interactions.

Further, different qualities of alarm levels can be implemented to allow the user to differentiate between vital signs patient status and closed loop controller alarms. The configurations for the different alarming conditions can be matched, combined alarms of physiological and closed loop controller alarms can be generated to optimize and reduce the necessary interaction with the patient monitor for the user. Thus, the patient is supervised and controlled only by one device, i.e. the integrated patient monitor and closed loop controller device.

BRIEF DESCRIPTION OF THE DRAWINGS

These and other aspects of the invention will be apparent from and elucidated with reference to the embodiments described hereinafter.

In the drawings the FIGURE schematically depicts a system for monitoring and controlling a patient according to a preferred embodiment of the invention.

DETAILED DESCRIPTION OF EMBODIMENTS

Based on above definition of a patient monitor, the following functionalities are implemented in a patient monitor according to a preferred embodiment of the invention in order to realize an integrated closed loop controller:

The integrated closed loop controller and, thus, the patient monitor is provided with a closed loop control algorithm. Further, special filtering and algorithms to process the input signals, with the intention to generate optimized inputs for the internal closed loop controller and support closed loop controller decisions are provided. Data capturing of input raw signals, internally processed signals, output signals and closed loop controller state. e.g. real time and trend, is provided in order to document and visualize the closed loop controller algorithm decisions Moreover, configure and setup vital alarms, closed loop controller alarms and/or combined alarms, e.g. using predefined events are provided. Such predefined events are defined by multi parameter alarm conditions, which means that at least two different parameters have to fall into a respective predefined range, have to exceed a respective predefined threshold or have to fall under a respective predefined threshold. The configurations for the different alarming conditions can be matched. A unique user interface is used for vital signs and closed loop controller user interactions.

Implementing a supervised closed loop controller in a patient monitor includes the implementation of an open loop controller and dynamic transitions between to these two controller types. The open loop controller can be also be run standalone as an advisory and documentation system, without the requirement to work in a closed loop environment. The current state of the closed loop control is always logged together with the physiological variables.

The closed loop analyzes the physiologic feedback signals and generates a control signal automatically. The following are reasons for fallback to open loop controller mode: One or more feedback signals are outside the predefined limits, one or more feedback signals can no longer be measured, or the measurement quality is insufficient, the controller detects that the a change in the controlling signal does no longer influence the feedback signals. The fallback to open loop controller mode is additionally announced as a predefined alarming condition.

Supervised closed loop is similar to the closed loop, wherein the output of the closed loop controller is controlled, preferably visually, by the user, allowing him to acknowledge the controller output change, and to switch manually to open loop mode to overwrite the controller output manually. The open loop analyzes the physiologic feedback signals with the intention to give advisory to the user, i.e. care giver, waiting for interaction and decisions of the user and still documenting time-synchronous all commands, proposed and user controller output and physiological feedback variables for a clinical decision support system. The proposed controller output and the manually adjusted output by the user can, but do not have to, match which each other.

The inventions can be used in various, preferably closed loop control systems. One of ordinary skill in the art will recognize that the purpose of controlling is not limited to a single type of control loop and includes several variations and different implementations of control loops, e.g. closed loop controls, supervised controls and open loop controls. Examples are: FiO2 control, infusion pumps medication control, e.g. to control the blood pressure of a patient, control for depth of anaesthesia, e.g. control of intravenous-aesthetic agents during non-volatile anaesthesia procedures, and glycemic control.

For elucidation of the principles of the invention, referring to the FIGURE, in the following a system is described as a preferred embodiment of the invention, wherein the SaO2 value of a patient is controlled by adjusting the FiO2 concentration of the gas mixture that is provided to the patient. For example, this can be implemented in a closed loop control of blood oxygen saturation in premature infants.

As depicted in the FIGURE, according to the preferred embodiment of the invention, a system for monitoring and controlling a patient 1, is provided which comprises a patient sensor 2 for capturing a patient signal. The system further comprises a patient monitor 3 with an integrated closed loop controller 4 which is fed with the patient signal and which controls a patient treating device 5, in the present case a mechanical ventilator, for treating the patient 1, i.e. for providing the patient 1 with oxygen.

Further, a user interface 6 is provided. This user interface 6 is adapted indicating information, e.g. information on the patient 1, on a display 7. Furthermore, the user interface 6 comprises an input device 8, like a keyboard or a touch screen which can be identical with the display 7, which allows a user to input data. Requests for such data input by the user can be indicated via the display 7.

Furthermore, a monitoring processer 9 for processing the patient signal and for outputting processed data to the user interface 6, and a control processer 10 for processing the patient signal and for outputting processed data to the closed loop controller 4, are provided. As can be seen from the FIGURE, the monitoring processer 9 and the control processer 10 are fed with the same patient signal in the same pre-processing state. The system also comprises an alarming unit 11 which is fed with the patient signal and which is adapted for providing common alarm conditions for monitoring and controlling, e.g. via display 7.

In the closed loop case, i.e. under normal conditions, FiO2 is controlled automatically, i.e. closed loop control is performed. This means that control is exclusively performed by the closed loop controller 4. The display is only used for indicating monitoring data and no external data input is requested.

Due to intentionally induced changes in the FiO2 value and/or due to changes of the FiO2 value due to normal control activities, according changes in the captured SpO2 value are expected. This feedback is continuously kept under surveillance, and based on this feedback, there are the following actions of the system:

1. The current model of the transfer functions is confirmed within acceptable limits and, thus, no adjustments of the model are necessary.

2. The response does not match with the current model of the transfer functions, but the deviations are in a range that allows to automatically adjusting the model of the transfer functions accordingly. Optionally the user might get a low priority warning in regards to the model changes so the user can verify what triggered the changes of the transfer function and might want to correct those. For example, the O2 uptake of the lung is reduced due to accumulation of secretion, but with a slightly increase FiO2 level this can be compensated. As the care giver could improve the situation by sucking the patient airways this would trigger a medium or low urgency notification to the user.

3. The response does not match with the current model of the transfer functions and the deviations are so extreme or do not fit into the model that an automatically adjustment of the model is not feasible or too risky. In this case the user is informed of this situation with a higher urgency. The urgency level might also depend on the actual state of the patient variable, but in any case it is important the user is aware of the situation as it might be impossible for the closed loop system to properly react on potential degradation of the patient's conditions in the future. For example, due to airway obstruction there is nearly no air reaching the lungs so the SaO2 will drop quickly even when the FiO2 is set to the maximum. This is a change in the transfer function of the patient that cannot be compensated by the closed loop control system.

Accordingly, a high urgency notification is triggered to the user. According to another example, the O2 supply for the patient got disconnected and the patient is breathing room air. Depending on the current patients condition this might cause only a slight drop of SaO2 that might still be in the acceptable range, but the closed loop controller has no control anymore to provide higher FiO2 levels if the patient might require it in the future. This triggers a medium urgency notification to the user.

However, in all these cases in which the response does not match with the current model of the transfer functions and the deviations are so extreme or do not fit into the model that an automatically adjustment of the model is not feasible or too risky, a change from closed loop to open loop is performed and input of external data from a user is requested.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A system for monitoring a patient and controlling patient treatment, the system comprising:
   a patient sensor for capturing a patient signal;
   a user interface for providing a user with information on the captured patient signal;

an integrated closed loop controller which is fed with the patient signal in a processed state and which controls a patient treating device for treating the patient, wherein the integrated closed loop controller includes a transfer function model controlling the patient treating device based on an input target value for the patient signal, wherein the transfer function model is dynamical adjusted based on deviations between the input target value and an output value of the patient signal, and wherein the user is provided with a warning in response to dynamic adjustment of the transfer function model;

a monitoring processer for processing the patient signal and for outputting processed data to the user interface; and a control processer for processing the patient signal and for outputting the patient signal in the processed state to the integrated closed loop controller, wherein the monitoring processer and the control processer are fed with the same patient signal in the same pre-processing state.

2. The system according to claim 1, further comprising:
an alarming unit, independent of the monitoring processor and the control processor, which is fed with the patient signal in the pre-processing state and which is adapted for providing common alarm conditions for monitoring and controlling.

3. The system according to claim 1, wherein the user interface is adapted for indicating and/or inputting monitoring data and control data.

4. The system according to claim 3, wherein the user interface is adapted for requesting the user to input external data as input data for the closed loop controller.

5. The system according to claim 1, wherein the control processor applies a filtering algorithm to the patient signal to generate the processed data, wherein the filtering algorithm optimizes the patient signal for the integrated closed loop controller.

6. The system according to claim 1, further including an alarming unit which provides a warning in response to the dynamic adjustment of the transfer function model being impossible or of a risk level to the patient exceeding a threshold.

7. A method for monitoring and controlling a patient, said method comprising:
capturing a patient signal with a patient sensor;
processing, by a monitoring processor, the patient signal for a monitoring purpose to generate monitoring data for display on a patient monitor;
displaying the monitoring data on a user interface;
processing, by a control processor independent of the monitoring processor, the patient signal for a control purpose to generate control data, wherein processing the patient signal for the monitoring purpose and processing the patient signal for the control purpose are based on the same patient signal in the same pre-processing state;
feeding a closed loop controller with the control data; and,
controlling, by the closed loop controller, a patient treatment device for treating the patient, the patient treatment device controlled using a transfer function model of the closed loop controller; and
dynamically adjusting the transfer function model based on deviations between an input target value and an output value of the patient signal, wherein the user is provided with a warning in response to dynamic adjustment of the transfer function model.

8. The method according to claim 7, further comprising:
processing the patient signal in the pre-processing state to determine common alarm conditions for monitoring and controlling, independent of processing the patient signal for the monitoring purpose and processing the patient signal for the control purpose.

9. The method according to claim 7, further comprising:
using a common user interface for indicating and/or inputting monitoring data and control data.

10. The method according to claim 9, further comprising:
requesting a user to input external data required as input data for the closed loop controller via the common user interface.

11. The method according to claim 7, wherein controlling the treatment of the patient is based on an input value, said method further comprising:
comparing the input value to an output value of the captured patient signal; and,
generating a further action if the output value deviates from an expected output value by more than a predefined amount.

12. The method according to claim 11, wherein the further action is an alarm and/or fallback to an open loop control.

13. The method according to claim 11, wherein the input value is intentionally varied.

14. The method according to claim 7, wherein the user is provided with a warning in response to dynamic adjustment of the transfer function model.

15. The method according to claim 7, wherein the transfer function includes an input, an output, and one or more parameters modeling the relationship between the input and the output, wherein dynamically adjusting the transfer function model includes dynamically adjusting the parameters.

16. The method according to claim 7, further including:
filtering the patient signal in the pre-processed state using a filtering algorithm, wherein the filtering algorithm optimizes the patient signal for the closed loop controller; and,
feeding the closed loop controller with the filtered patient signal, wherein the closed loop controller controls the treatment of the patient based on the filtered patient signal.

17. A system for monitoring a patient and controlling a patient treatment, said system comprising:
at least one patient sensor which generates one or more patient signals indicative of a plurality of physiological parameters of the patient;
a user interface which displays information on the patient parameters to a user;
a patient treating device which administers a treatment to the patient;
a monitoring processer which processes the patient signal for display and outputs monitoring data to the user interface for display;
a control processer which processes the patient signal concurrently with the monitoring processer for controlling the patient treatment device and outputs control data;
an integrated closed loop controller which receives the control data from the control processor and which controls the patient treating device based on a transfer function model of the integrated controller, the transfer function model dynamically adjusted based on the control data from the control processor; wherein the user is provided with a warning in response to dynamic adjustment of the transfer function model;
an alarming unit, independent of the monitoring processor and the control processor, which is fed with the patient signal in the same pre-processing state as the control processor and the monitoring processor and which is adapted for providing common alarm conditions for monitoring and controlling.

18. The system according to claim 17, wherein the control processor applies a filtering algorithm to the patient signal in the pre-processed state to generate the control data to adapt the patient signal for the integrated closed loop controller.

* * * * *